United States Patent [19]

Hummerich et al.

[11] 4,393,207
[45] Jul. 12, 1983

[54] ALKOXYALKYLAMINOTRIAZINE TRANS-ETHERIFICATION PRODUCTS

[75] Inventors: Rainer Hummerich, Ludwigshafen; Wolfram Weiss, Mutterstadt; Franz Merger, Frankenthal; Guenther Immel, Weinheim; Hans-Joachim Kraus, Ludwigshafen; Karl-Clemens Peters, Bad Durkheim, all of Fed. Rep. of Germany

[73] Assignee: BASF Aktiengesellschaft, Ludwigshafen, Fed. Rep. of Germany

[21] Appl. No.: 279,586

[22] Filed: Jul. 1, 1981

[30] Foreign Application Priority Data

Jul. 4, 1980 [DE] Fed. Rep. of Germany ....... 3025352

[51] Int. Cl.³ .................. C07D 251/70; C07D 251/18
[52] U.S. Cl. .................................. 544/196; 544/197; 544/205; 544/206
[58] Field of Search ................ 544/205, 206, 146, 147

[56] References Cited

U.S. PATENT DOCUMENTS

| | | | |
|---|---|---|---|
| 2,197,357 | 4/1940 | Widmer et al. | 544/197 |
| 2,953,536 | 9/1960 | Coidmer | 260/21 |
| 3,145,207 | 8/1964 | Wohnsiedler | 260/249.6 |
| 3,519,627 | 7/1970 | Coats et al. | 260/249.6 |

FOREIGN PATENT DOCUMENTS

| | | |
|---|---|---|
| 1102384 | 2/1968 | United Kingdom . |
| 1268481 | 3/1972 | United Kingdom . |
| 1273616 | 5/1972 | United Kingdom . |
| 1320387 | 6/1973 | United Kingdom . |
| 1440166 | 6/1976 | United Kingdom . |
| 1465426 | 2/1977 | United Kingdom . |
| 1535826 | 12/1978 | United Kingdom . |

Primary Examiner—John M. Ford
Attorney, Agent, or Firm—Keil & Witherspoon

[57] ABSTRACT

Alkoxyalkylaminotriazine trans-etherification products are obtained by reacting an alkoxyalkylaminotriazine of the general formula

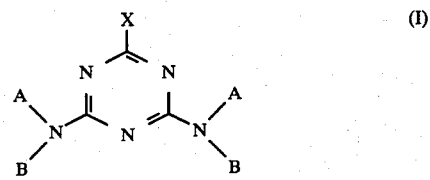

where X is hydrogen, alkyl, phenyl, alkylphenyl or

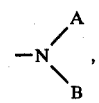

A and B are hydrogen, alkyl, alkenyl or

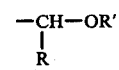

and R and R' are hydrogen or alkyl, with from 0.1 to 6 moles, per mole of alkoxyalkylaminotriazine, of a β-hydroxyaldehyde of the general formula

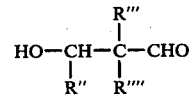

where R'', R''' and R'''' are identical or different and each is hydrogen or alkyl or R''' and R'''' together with the α-carbon atom form a cyclopentane or cyclohexane ring, and R''' and/or R'''' can also be hydroxyalkyl and R'''' can also be phenyl, in the presence of an acidic catalyst, and removing the alcohol resulting from the trans-etherification. The alkoxyalkylaminotriazine trans-etherification products may be used in baking finishes and acid-hardening surface coatings.

5 Claims, No Drawings

ALKOXYALKYLAMINOTRIAZINE TRANS-ETHERIFICATION PRODUCTS

The present invention relates to alkoxyalkylaminotriazine trans-etherification products which are obtained from alkoxyalkylaminotriazines and β-hydroxyaldehydes.

Alkoxyalkylaminotriazines, for example tetramethoxymethylguanamines and hexamethoxymethylmelamine, have long been known. The last-mentioned compound is obtained, for example, by condensing 1 mole of melamine with 6 moles of formaldehyde to give hexamethylolmelamine and then completely etherifying this product with 6 moles of methanol to give the hexamethoxymethyl derivative. Compounds of this type are known as highly reactive surface-coating resins and can be crosslinked with a plurality of hydroxyl-containing, carboxyl-containing and amide-containing polymers.

Further, it is known that these compounds can be trans-etherified with other alcohols in the presence of an acidic catalyst, giving compounds containing additional functional groups. Such trans-etherification reactions are disclosed, for example, in the following publications (the alcohol component being shown in parentheses): German Published Application DAS No. 2,414,426 (methylglycol), Netherlands Pat. No. 6,614,313 (hydroxystearic acid), U.S. Pat. No. 3,519,627 (dimethylolpropionic acid or glyoxylic acid), British Pat. No. 1,268,481 (allyl alcohol), Swiss Pat. No. 362,527 (but-2-en-1-ol), U.S. Pat. No. 3,145,207 (epoxyalcohols) and German Published Application DAS No. 2,327,147 (cyclohexanol).

In all cases, products having novel, specific properties are obtained.

It is an object of the present invention to provide novel alkoxyalkylaminotriazine trans-etherification products, which not only can be prepared very advantageously but also exhibit very valuable use characteristics.

We have found that this object is achieved, according to the invention, by providing alkoxyalkylaminotriazine trans-etherification products which are obtained by reacting an alkoxyalkylaminotriazine of the general formula (I)

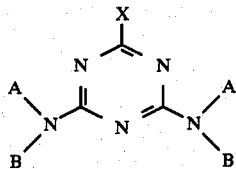

where X is hydrogen, alkyl of 1 to 15 carbon atoms, phenyl, alkylphenyl, where alkyl is of 1 to 4 carbon atoms, or

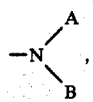

A and B are identical or different and each is hydrogen, alkyl of 1 to 4 carbon atoms, alkenyl of 3 to 15 carbon atoms or $$-\text{CH}-\text{OR}',\\ \phantom{-\text{CH}-}|\\ \phantom{-\text{CH}-}R$$

and R and R' are identical or different and each is hydrogen or alkyl of 1 to 9 carbon atoms, with from 0.1 to 6 moles, per mole of alkoxyalkylaminotriazine, of a β-hydroxyaldehyde of the general formula (II)

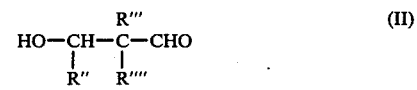

where R'', R''' and R'''' are identical or different and each is hydrogen or alkyl of 1 to 5 carbon atoms or R''' and R'''' together with the α-carbon atom form a cyclopentane or cyclohexane ring, and R''' and/or R'''' can also be hydroxyalkyl of 1 to 4 carbon atoms and R'''' can also be phenyl, in the presence of an acidic catalyst, and removing the alcohol resulting from the trans-etherification.

The present invention also relates to the use of these trans-etherification products in surface coatings.

As regards the synthesis components, and method of preparation, of the novel trans-etherification products, the following details may be noted.

Examples of alkoxyalkylaminotriazines of the above general formula (I) are the corresponding derivatives of melamine, guanamine, benzoguanamine and acetoguanamine, e.g. hexamethoxymethylmelamine, hexabutoxymethylmelamine, tetramethoxybenzoguanamine, tetramethoxyacetoguanamine, tetramethoxy-N,N-dialkylmelamine and N,N',N''-trimethoxyisobutylmelamine. It is also possible to use advantageously commercial products of this type, for example industrially produced hexamethoxymethylaminotriazine in which the methoxy groups may in part be replaced by hydrogen or by other low molecular weight alkoxy groups, for example by ethoxy, propoxy or butoxy.

Suitable β-hydroxyaldehydes of the above general formula (II) are, in general, aldol adducts obtainable according to the following equation:

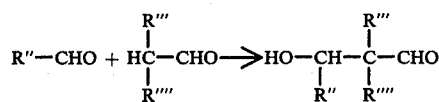

Examples of aldehydes which may be used for this reaction are formaldehyde, acetaldehyde, propanal, n-butanal, n-pentanal, n-hexanal, n-heptanal, 2-methylpropanal, 2-methylbutanal, 2-methylpentanal, 2-ethylbutanal, 2-ethylhexanal, 3-methylbutanal, cyclopentyl-carboxaldehyde and cyclohexyl-carbaldehyde.

β-Hydroxyaldehydes obtainable by this reaction include, for example, 3-hydroxybutanal, 3-hydroxy-2-methyl-propanal, 3-hydroxy-2-methyl-butanal, 3-hydroxy-2-methyl-pentanal, 3-hydroxy-2-methyl-hexanal, 3-hydroxy-2-methyl-heptanal, 3-hydroxy-2-ethylpentanal and 3-hydroxy-2-ethyl-hexanal, and especially the reaction products of iso-alkanals and n-alkanals or cycloalkyl-carboxaldehydes with formaldehyde, eg. 2,2-dimethyl-3-hydroxy-propanal, 2-methyl-2-ethyl-3-hydroxy-propanal, 2-methyl-2-propyl-3-hydroxypropanal, 2-ethyl-2-butyl-3-hydroxypropanal, 2,2-dimethylol-propanal, 2,2-dimethylol-butanal, 2,2-dimethylol-pentanal, 2,2-dimethylol-3-hydroxy-propanal, 1-methylol-cyclopentyl-carboxaldehyde and 1-methylol-cyclohexyl-carboxaldehyde. Processes for the preparation of these products are described, inter alia, in German Published Application DAS No. 1,793,512 and German Laid-Open Applications DOS No. 1,957,301 and DOS No. 2,507,461. An example of a preferred compound is 2,2-dimethyl-3-hydroxypropanal (hydroxypivalaldehyde), where $R''=H$, and $R'''=R''''=CH_3$.

According to the invention, from 0.1 to 6, preferably from 0.5 to 4.5, moles of the $\beta$-hydroxyaldehyde are employed per mole of alkoxyalkylaminotriazine.

The reaction according to the invention is carried out in the presence of an acidic catalyst, such as an inorganic or organic acid, eg. HCl, $H_2SO_4$, $H_3PO_4$, p-toluenesulfonic acid, oxalic acid or maleic acid, or of maleic anhydride or of an acidic ion exchanger, in the presence or absence of a solvent, such as an aliphatic or cycloaliphatic hydrocarbon, e.g. an n-alkane or cyclohexane, or an aromatic hydrocarbon, e.g. toluene or xylene, in general at from 50° to 150° C., preferably from 60° to 120° C.

The following are examples of different embodiments of the process for the preparation of the novel trans-etherification products.

PROCESS 1

A $\beta$-hydroxyaldehyde is dissolved in cyclohexane. Any water present is then removed by azeotropic distillation. The alkoxyalkylaminotriazine, and the acid (for example p-toluenesulfonic acid) are added to the solution. The alcohol formed in the reaction is then removed by azeotropic distillation. The mixture is cooled to room temperature and is neutralized with a calculated amount of a base (for example NaOH). It is then diluted, for example with toluene, and filtered, advantageously by means of a pressure filter after having added a filtration aid. The clear filtrate can be concentrated under reduced pressure to the desired solids content.

PROCESS 2

This is carried out like process 1, except that toluene is used directly as the solvent. Accordingly, water is introduced initially into the vessel in order to separate off the alcohol formed.

PROCESS 3 (without solvent)

A $\beta$-hydroxyaldehyde is mixed with an alkoxyalkylaminotriazine at 65° C. After adding an acid, the alcohol formed is distilled off in the course of 30–180 minutes under reduced pressure at 80°–100° C. The reaction mixture is then diluted with a solvent, for example toluene or xylene, and neutralized with a calculated amount of a base (for example NaOH), after which the salt is filtered off. The clear filtrate can be brought to any desired solids content.

The alkoxyalkylaminotriazine trans-etherification products according to the invention can also be used very advantageously for the preparation of secondary products formed, for example, by chemical modification of the aldehyde group in (I), such as by oxidation, reduction, disproportionation or condensation with a nucleophilic agent. The secondary reaction can take place during the trans-etherification reaction or be effected in a separate process step after the trans-etherification.

The products according to the invention prove to be useful as components in both acid-hardening surface coatings and in baking finishes; for example they serve as binders having surprisingly good properties.

The Examples which follow illustrate the preparation of the products according to the invention, and their use. In the Examples, parts and percentages are by weight, unless stated otherwise.

PREPARATION OF THE $\beta$-HYDROXYALDEHYDES

The $\beta$-hydroxyaldehydes required for the reaction can be prepared, inter alia, by the methods described in German Laid-Open Applications DOS No. 1,957,301 and DOS No. 2,507,461 and German Published Application DAS No. 1,793,512. With a view to the reaction with an alkoxyalkylaminotriazine, it is particularly advantageous to prepare the $\beta$-hydroxyaldehyde in situ, for example as follows:

734.7 parts of isobutyraldehyde are mixed with 750 parts of 40% strength formaldehyde, whilst stirring. After the mixture has been heated to about 40° C., 25.7 parts of 40% strength trimethylamine are run in. The temperature is allowed to rise to 45° C. and cooling is then applied so that the temperature thereafter rises only slowly to 60° C. A further 8.6 parts of 40% strength trimethylamine are then added and the reaction is controlled so that the temperature only rises slowly to 75°–80° C. and the solution does not come to the boil. The mixture is then quickly heated to 90°–92° C. and immediately cooled again to 65°–70° C. Thereafter the reaction solution is concentrated under reduced pressure from a waterpump, and at an internal temperature of 65° C., until the first drops of hydroxypivalaldehyde pass over. This is the case at a bottom temperature of 90° C. and a boiling point of 75° C. under the lowest pressure obtainable from a waterpump.

The $\beta$-hydroxyaldehyde thus obtained is then reacted with an alkoxyalkylaminotriazine by one of the above three processes, either in the same reaction vessel as that in which the $\beta$-hydroxyaldehyde has been prepared or in a separate vessel.

EXAMPLES 1 TO 41

The solids contents and viscosities shown in the Tables were determined as follows:
Solids content:
  2 g of resin solution are dried for 2 hours at 120° C. in a through-circulation dryer and the residue is then weighed.
Viscosity:
  The dynamic viscosity was determined at 20° C. in a rotary viscometer (for example a Rotavisko from Haake).
HMMM = hexamethoxymethylmelamine
HPA = hydroxypivalaldehyde

TABLE 1

Reactions of HMMM with $HOCH_2-\underset{\underset{C_2H_5}{|}}{\overset{\overset{CH_3}{|}}{C}}-CHO$ (I) or $HOCH_2-\underset{\underset{C_3H_7}{|}}{\overset{\overset{CH_3}{|}}{C}}-CHO$ (II)

| Example No. | Process | Alkoxyalkylaminotriazine | Parts | β-hydroxyaldehyde | Parts | Acid | Parts | Appearance | solids content | Viscosity at 20° C. |
|---|---|---|---|---|---|---|---|---|---|---|
| 1 | 1 | $X=N\underset{B}{\overset{A}{\diagdown}}$ ; A=B=$CH_2-OCH_3$ = HMMM | 195 | I | 232 | p-toluenesulfonic acid | 5 | clear solution; | 59.6%; | 18 mPa.s |
| 2 | 1 | HMMM | 260 | I | 232 | p-toluenesulfonic acid | 5 | clear solution; | 59.4%; | 28 mPa.s |
| 3 | 1 | HMMM | 312 | I | 232 | p-toluenesulfonic acid | 5 | clear solution; | 68.3%; | 26 mPa.s |
| 4 | 1 | HMMM | 390 | I | 232 | p-toluenesulfonic acid | 5 | clear solution; | 64.3%; | 32 mPa.s |
| 5 | 1 | HMMM | 180 | II | 240 | p-toluenesulfonic acid | 4.6 | clear solution; | 67.9%; | 12 mPa.s |
| 6 | 1 | HMMM | 240 | II | 240 | p-toluenesulfonic acid | 4.6 | clear solution; | 71%; | 17 mPa.s |
| 7 | 1 | HMMM | 288 | II | 240 | p-toluenesulfonic acid | 4.6 | clear solution; | 71%; | 19 mPa.s |
| 8 | 1 | HMMM | 360 | II | 240 | p-toluenesulfonic acid | 4.6 | clear solution; | 73.6%; | 24 mPa.s |
| 9 | 1 | HMMM | 195 | II | 260 | p-toluenesulfonic acid | 5 | clear solution; | 60%; | 1,700 mPa.s |

TABLE 2

Reactions of HMMM with an aqueous solution of HPA

| Example No. | Process | Alkoxyalkylaminotriazine | Parts | β-Hydroxyaldehyde | Parts | Acid | Parts | Appearance | solids content |
|---|---|---|---|---|---|---|---|---|---|
| 10 | 1 | $X=N\underset{B}{\overset{A}{\diagdown}}$ ; A=B=$CH_2OCH_3$ = HMMM | 772 | $HOCH_2-\underset{\underset{CH_3}{|}}{\overset{\overset{CH_3}{|}}{C}}-CHO$ = HPA (72.1% strength) | 140 | p-toluenesulfonic acid | 5 | clear solution; | 47.7% in toluene |
| 11 | 1 | HMMM | 772 | HPA (72.1% strength) | 280 | p-toluenesulfonic acid | 10 | clear solution; | 51.74% in toluene |
| 12 | 1 | HMMM | 397 | HPA (83.2% strength) | 250 | p-toluenesulfonic acid | 10 | clear solution; | 50.2% in toluene |
| 13 | 1 | HMMM | 318 | HPA (83.2% strength) | 250 | p-toluenesulfonic acid | 10 | clear solution; | 50.22% in toluene |
| 14 | 1 | HMMM | 265 | HPA (83.2% strength) | 250 | p-toluenesulfonic acid | 10 | clear solution; | 53.95% in toluene |
| 15 | 2 | HMMM | 841 | HPA (78.6% strength) | 140 | p-toluenesulfonic acid | 5 | clear solution; | 49.3% |
| 16 | 2 | HMMM | 841 | HPA (78.6% strength) | 280 | p-toluenesulfonic acid | 10 | clear solution; | 49.89% |
| 17 | 2 | HMMM | 420 | HPA (78.6% strength) | 280 | p-toluenesulfonic acid | 10 | clear solution; | 50.92% |

TABLE 3

Reactions of tetrakis-methoxymethyl-benzoguanamine (III)

| Example No. | Process | Alkoxyalkylamino-triazine | Parts | β-Hydroxyaldehyde | Parts | Acid | Parts | Appearance | Solids content | Viscosity at 30° C. |
|---|---|---|---|---|---|---|---|---|---|---|
| 18 | 1 | X = Phenyl; A=B=CH$_2$OCH$_3$ = III | 92.5 | HOCH$_2$—C(CH$_3$)(CH$_3$)—CHO (HPA) (77% strength) | 135 | p-toluene-sulfonic acid | 2.5 | clear solution; | 48% strength in toluene | |
| 19 | 1 | III | 185 | HPA (77% strength) | 135 | p-toluene-sulfonic acid | 2.5 | clear solution; | 63.4% strength in toluene | 220 mPa.s |
| 20 | 1 | III | 123 | HPA (77% strength) | 135 | p-toluene-sulfonic acid | 2.5 | clear solution; | 32.9% strength in cyclohexane | |
| 21 | 2 | III | 181.5 | HOCH$_2$—C(CH$_2$OH)(CH$_3$)—CHO (29.5% strength) | 200 | p-toluene-sulfonic acid | 1.125 | clear solution; | 56.1% strength in toluene | |
| 22 | 3 | III | 302 | HOCH$_2$—C(CH$_3$)(C$_2$H$_5$)—CHO | 290 | p-toluene-sulfonic acid | 6.25 | | 76.4% | 732 mPa.s |
| 23 | 3 | III | 227 | " | 290 | p-toluene-sulfonic acid | 6.25 | | 69.4% | 304 mPa.s |
| 24 | 3 | III | 302 | HOCH$_3$—C(CH$_3$)(C$_3$H$_7$)—CHO | 325 | p-toluene-sulfonic acid | 6.25 | | 69.4% | 165 mPa.s |
| 25 | 3 | III | 227 | " | 304 | p-toluene-sulfonic acid | 6.25 | | 67.7% | 347 mPa.s |

TABLE 4

Effect of varying the HMMM:HPA ratio

| Example No. | Process | Alkoxyalkylamino-triazine | Parts | β-Hydroxyaldehyde | Parts | Acid | Parts | Appearance | Solids content | Viscosity at 30° C. |
|---|---|---|---|---|---|---|---|---|---|---|
| 26 | 3 | X=N(A)(B); A=B=CH$_2$OCH$_3$ = HMMM | 1040 | HOCH$_2$—C(CH$_3$)(CH$_3$)—CHO (HPA) | 408 | p-toluene-sulfonic acid | 10 | clear solution; | 85%; | 22,224 mPa.s |
| 27 | 3 | HMMM | 891 | HPA | 408 | p-toluene-sulfonic acid | 10 | clear solution; | 81.2%; | 4,145 mPa.s |
| 28 | 3 | HMMM | 693 | HPA | 408 | p-toluene-sulfonic acid | 10 | clear solution; | 80.8%; | 7,086 mPa.s |
| 29 | 3 | HMMM | 624 | HPA | 408 | p-toluene-sulfonic acid | 10 | clear solution; | 86.4%; | 30,337 mPa.s |
| 30 | 3 | HMMM | 780 | HPA | 408 | p-toluene-sulfonic acid | 10 | clear solution; | 71.4%; | 2,161 mPa.s |
| 31 | 3 | HMMM | 1040 | HPA | 408 | p-toluene-sulfonic acid | 10 | clear solution; | 72.6%; | 420 mPa.s |

TABLE 5

Reactions of HMMM with various β-hydroxyaldehydes

| Example No. | Process | Alkoxyalkylamino-triazine | Parts | β-Hydroxyaldehyde | Parts | Acid | Parts | Appearance | Solids content | Viscosity at 20 or 30° C. |
|---|---|---|---|---|---|---|---|---|---|---|
| 32 | 3 | $X=N{\begin{smallmatrix}A\\B\end{smallmatrix}}$ ; $A=B=CH_2OCH_3$ = HMMM | 1040 | $HO-CH_2-\underset{CH_3}{\underset{\|}{\overset{CH_3}{\overset{\|}{C}}}}-CHO$ (HPA) | 408 | p-toluene-sulfonic acid | 10 | clear solution; | 85%; | 22,224 mPa.s (at 30° C.) |
| 33 | 3 | HMMM | 780 | HPA | 408 | p-toluene-sulfonic acid | 10 | clear solution; | 85.1%; | 12,051 mPa.s (at 30° C.) |
| 34 | 3 | HMMM | 195 | $HO-CH_2-\underset{C_3H_7}{\underset{\|}{\overset{CH_3}{\overset{\|}{C}}}}-CHO$ | 260 | p-toluene-sulfonic acid | 5 | clear solution; | 76.6%; | 6,120 mPa.s (at 20° C.) |
| 35 | 3 | HMMM | 260 | " | 260 | p-toluene-sulfonic acid | 5 | clear solution; | 73.6%; | 4,800 mPa.s (at 20° C.) |
| 36 | 3 | HMMM | 520 | $HOCH_2-\underset{C_2H_5}{\underset{\|}{\overset{CH_3}{\overset{\|}{C}}}}-CHO$ | 464 | p-toluene-sulfonic acid | 10 | clear solution; | 73.9%; | 2,000 mPa.s (at 20° C.) |
| 37 | 3 | HMMM | 780 | " | 928 | p-toluene-sulfonic acid | 20 | clear solution; | 74.8%; | 7,532 mPa.s (at 30° C.) |
| 38 | 2 | HMMM | 780 | $HOCH_2-\underset{CH_3}{\underset{\|}{\overset{CH_2OH}{\overset{\|}{C}}}}-CHO$ (29.5% strength) | 400 | p-toluene-sulfonic acid | 2.25 | clear solution; | 57.4%; | |
| 39 | 2 | HMMM | 520 | " | 800 | p-toluene-sulfonic acid | 5 | clear solution; | 51.2%; | 400 mPa.s (at 20° C.) |
| 40 | 2 | HMMM | 260 | HPA | 204 | p-toluene-sulfonic acid | 5 | clear solution; | 68.4% | |
| 41 | 2 | HMMM | 390 | HPA | 204 | p-toluene-sulfonic acid | 5 | clear solution; | 70.9% | 420 mPa.s (at 30° C.) |

Use tests on some of the resin solutions of the Examples shown in Tables 1 to 5 are given below.

I. Baking finishes

Examples 41 to 51 show the advantage of the higher resilience (=better Erichsen deep-drawing value) compared to commercial melamine/formaldehyde resins, for the same hardness.

The commercial alkoxyalkylaminotriazine resin used was a butanol-etherified highly reactive melamine/formaldehyde resin in the form of an about 60% strength solution in butanol/xylene.

EXAMPLE 42

The resin solution prepared as described in Example 40 is used as the hardener for a finish in which the base resin is a polymeric acrylate resin composed of 46 parts of styrene, 37 parts of butyl acrylate, 15 parts of hydroxypropyl acrylate and 2 parts of acrylic acid as copolymerized units, the resin being in the form of a 60% strength solution in an 8:2 xylene/butanol mixture. The ratio of acrylate resin to amino resin (solids/solids) is 7:3.

Formulation A 58.3 parts of acrylate resin (60% strength solution in an 8:2 xylene/butanol mixture), 21.9 parts of the resin solution from Example 40 (68.4% strength in xylene), 50 parts of TiO$_2$ (®Kronos RN 57 from Titangesellschaft Leverkusen) and 20 parts of a xylene/ethylglycol mixture (8:2) are milled with about 100 parts of glass beads for about 20 minutes, in an apparatus which provides an intensive three-dimensional shaking motion (Red Devil, from Red Devil Inc., New Jersey). The mixture is sieved to remove the beads and the finish is diluted with xylene/ethylglycol to 20 seconds flow time in a DIN cup with 4 mm nozzle. It is then applied by means of a spray gun to 1 mm thick deep-drawn tin-plate, in an amount corresponding to a dry coating thickness of about 50 μm. After having been sprayed, the coated tinplate is air-dried for 5 minutes and is then baked for 30 minutes at 150° C. in a through-circulation dryer.

| Test results | |
|---|---|
| Gloss (Gardner method, 60°) | = 90% |
| Erichsen deep-drawing value | = 6.2 mm (DIN 53,156) |
| Pendulum hardness (König method) | = 182 s (DIN 53,157) |
| Cross-hatch test | = 2.5 (DIN 53,151) |

The comparative experiment with the commercial melamine-formaldehyde resin gives the following results under identical conditions:

| | |
|---|---|
| Gloss | = 83% |
| Erichsen deep-drawing value | = 2.6 mm |
| Pendulum hardness | = 157 s |
| Cross-hatch test | = 3 |

EXAMPLE 43

The same starting resin (see Example 40) is used in a modified formulation, the ratio of acrylate resin to amino resin (solids/solids) being 1:1.

Formulation B 41.7 parts of acrylate resin (60% strength in xylene), 36.5 parts of the resin solution from Example 40 (68.4% strength in xylene), 50 parts of TiO$_2$ (RN 57) and 20 parts of xylene/ethylglycol are milled with 100 parts of glass beads, as described above, and then processed further as previously described.

| | Test results | |
|---|---|---|
| | with product according to the invention | with commercial resin |
| Gloss | 88 | 83 |
| Erichsen deep-drawing value | 5.2 | 1.5 |
| Pendulum hardness | 179 | 162 |
| Cross-hatch test | 3 | 4 |

EXAMPLE 44

A finish is prepared from the resin solution of Example 30, using formulation B (i.e. a 1:1 ratio of acrylate to melamine-formaldehyde resin), and is applied, and baked, in the manner described above.

| | Test results | |
|---|---|---|
| | with product according to the invention | with commercial resin |
| Gloss | 88 | 90 |
| Erichsen deep-drawing value | 5.2 | 1.2 |
| Pendulum hardness | 188 | 165 |
| Cross-hatch test | 2.5 | 4 |

EXAMPLE 45

Using the resin solution prepared according to Example 30, a finish based on a synthetic fatty acid alkyd resin (for example ®Alkydal F 251 from Bayer, Leverkusen) is prepared in accordance with formulation B, i.e. the acrylate resin in formulation B is replaced by ®Alkydal.

| | Test results | |
|---|---|---|
| | with resin from Example 30 | with commercial resin |
| Gloss | 94 | 60 |
| Erichsen deep-drawing value | 4.0 | 0.6 |
| Pendulum hardness | 193 | 171 |
| Cross-hatch test | 3 | 4 |

EXAMPLE 46

The procedure described in Example 43 is followed, but using the resin from Example 31.

| | Test results | |
|---|---|---|
| | with product according to the invention | with commercial resin |
| Gloss | 86 | 90 |
| Erichsen deep-drawing value | 6.5 | 1.2 |
| Pendulum hardness | 167 | 165 |
| Cross-hatch test | 2 | 4 |

EXAMPLE 47

The procedure described in Example 45 is followed, but using the resin from Example 31.

| | Test results | |
|---|---|---|
| | with product according to the invention | with commercial resin |
| Gloss | 93 | 60 |
| Erichsen deep-drawing value | 7.3 | 0.6 |
| Pendulum hardness | 170 | 171 |
| Cross-hatch test | 2 | 4 |

EXAMPLE 48

The procedure described in Example 43 is followed, but using the resin from Example 1.

| | Test results | |
|---|---|---|
| | with product according to the invention | with commercial resin |
| Gloss | 81 | 83 |
| Erichsen deep-drawing value | 5.1 | 1.5 |
| Pendulum hardness | 186 | 162 |
| Cross-hatch test | 3 | 4 |

EXAMPLE 49

The procedure described in Example 43 is followed, but using the resin from Example 4.

| | Test results | |
|---|---|---|
| | with product according to the invention | with commercial resin |
| Gloss | 83 | 83 |
| Erichsen deep-drawing value | 6.5 | 1.5 |
| Pendulum hardness | 181 | 162 |
| Cross-hatch test | 3 | 4 |

EXAMPLE 50

The procedure described in Example 43 is followed, but using the resin from Example 6.

EXAMPLE 51

The procedure described in Example 43 is followed, but using the resin from Example 18.

| | Test results | | |
|---|---|---|---|
| | Example 51 | Example 50 | commercial resin |
| Gloss | 86 | 86 | 83 |
| Erichsen deep-drawing value | 4.5 | 3.2 | 1.5 |
| Pendulum hardness | 178 | 179 | 162 |
| Cross-hatch test | 2 | 3 | 4 |

II. Acid-hardening finishes

Urea resins can in general be used in acid-hardening finishes and in baking finishes.

In the case of melamine/formaldehyde resins, the highly methylolated and substantially etherified types exhibit little reactivity in baking finishes but are suitable for acid-hardening finishes.

Conversely, the melamine-formaldehyde resins which have been prepared with less formaldehyde and are only partially etherified are suitable for baking systems but not useful in acid-hardening finishes.

In contrast, the resins described in the Examples are suitable for use both in baking finishes and in acid-hardening finishes, as may be seen from the Examples which follow. The finishes used are prepared in accordance with the following general formulations.

Formulation C 50 parts of acrylate resin (60% strength in butanol/xylene)
29.2 parts of an alkoxyalkylaminotriazine resin according to the invention, or of a commercial product (68.4% strength in xylene)
50 parts of TiO$_2$ (RN 57)
20 parts of xylene/butanol (8:2)

Accordingly, the acrylate resin and the amino resin are employed in a ratio of 6:4 (solids/solids), and are pigmented with 100% of TiO$_2$ (based on binder). The finish is used in the manner described in connection with formulation A.

Formulation D 50 parts of castor oil alkyd (60% strength in xylene)
29.2 parts of an alkoxyalkylaminotriazine resin according to the invention, or of a commercial product (68.4% strength in xylene)
50 parts of TiO$_2$ (RN 57)
20 parts of xylene/butanol The ratio of castor oil alkyd to amino resin is 6:4 (solids/solids). The composition is pigmented with 100% of TiO$_2$, based on binder. The finish is used in the manner described in connection with formulation A.

Formulation E (for acid-hardening)

35 parts of castor oil alkyd (60% strength in xylene)
13.9 parts of an alkoxyalkylaminotriazine resin according to the invention, or of a commercial product (69% strength in xylene)
22.1 parts or a 2:1 ethanol/ethylglycol mixture
3 parts of p-toluenesulfonic acid (20% strength in ethanol), ie. 6% of acid, based on solid amino resin, are added.

The constituents of the acid-hardening finish are stirred until a homogeneous mixture is obtained, and finally the acid solution is incorporated. The finishes are applied to glass by means of a film spreader, at a wet thickness of 150 μm, and kept for 30 minutes at 40° C. Before carrying out the König pendulum hardness test, the test plates are stored for 24 hours under standard humidity conditions at 23° C.

| Test results: Konig pendulum hardness (in seconds) | | | |
|---|---|---|---|
| Resin used | Formulation C | Formulation D | Formulation E acid-hardening finish |
| Example 52: from Example 40 | 182 | 198 | 171 |
| Example 53: from Example 1 | 174 | 179 | 157 |
| Example 54: from Example 5 | 171 | 182 | 120 |
| Example 55: from Example 14 | 186 | 197 | 155 |
| Example 56: from Example 13 | 185 | 197 | 174 |
| Commercial acid-hardening melamine resin | 38 | 28 | 150 |
| Commercial melamine baking resin | 162 | 175 | 40 |

To obtain a measure of the rate of hardening of acid-hardening finishes it is also possible to employ, in place of the König pendulum method, and Kempf test based on DIN 53,159, using the Kempf instrument from Erichsen GmbH. The following formulation was used when applying the Kempf test:

Formulation F 70 parts of a castor oil alkyd (60% strength in xylene)
19 parts (solids) of an alkoxyalkylaminotriazine resin according to the invention, or of a commercial product
53 parts of a 2:1 ethanol/ethylglycol mixture
12 parts of a p-toluenesulfonic acid solution (10% strength in ethanol)

The finishes are applied by the method described earlier.

| | | Test results | | | | | |
|---|---|---|---|---|---|---|---|
| | | Cycle time at 40° C. | | | | | |
| | Resin used | 5' | 10' | 15' | 20' | 25' | 30' |
| Example | | | | | | | |
| 57 | from Example 40 | 3–4 | 2 | 0 | 0 | 0 | 0 |
| 58 | from Example 1 | 1–2 | 0 | 0 | 0 | 0 | 0 |
| 59 | from Example 5 | 2–3 | 0–1 | 0 | 0 | 0 | 0 |
| 60 | from Example 14 | 1–2 | 0 | 0 | 0 | 0 | 0 |
| 61 | from Example 13 | 1 | 0 | 0 | 0 | 0 | 0 |
| Comparative Experiments | | | | | | | |
| | commercial | | | | | | |

| | Test results | | | | | |
|---|---|---|---|---|---|---|
| | Cycle time at 40° C. | | | | | |
| Resin used | 5' | 10' | 15' | 20' | 25' | 30' |
| AH-MF resin commercial | 4 | 4 | 3-4 | 3 | 2-3 | 2 |
| MF baking resin commercial | 5 | 5 | 5 | 5 | 5 | 5 |
| AH-UF resin | 1-2 | 0 | 0 | 0 | 0 | 0 |

0 = tack-free
5 = still very tacky
MF resin = melamine-formaldehyde resin
AH-MF resin = acid-hardening melamine-formaldehyde resin
AH-UF resin = acid-hardening urea-formaldehyde resin

We claim:

1. An alkoxyalkylaminotriazine trans-etherification product suitable for use in baking finishes or acid-hardening finishes, which is obtained by reacting an alkoxyalkylaminotriazine of the formula (I)

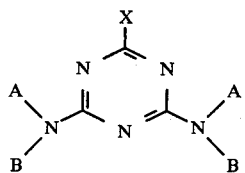 (I)

where X is hydrogen, alkyl of 1 to 15 carbon atoms, phenyl, alkylphenyl, where alkyl is of 1 to 4 carbon atoms, or

A and B are identical or different and each is hydrogen, alkyl of 1 to 4 carbon atoms, alkenyl of 3 to 15 carbon atoms or $$-\text{CH}-\text{OR}',$$
$$\phantom{-\text{CH}-}\text{R}$$

and R and R' are identical or different and each is hydrogen or alkyl of 1 to 9 carbon atoms, with from 0.1 to 6 moles, per mole of alkoxyalkylaminotriazine, of a β-hydroxyaldehyde of the general formula (II)

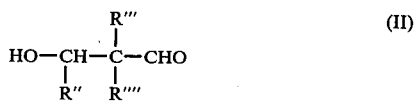 (II)

where R'', R''' and R'''' are identical or different and each is hydrogen or alkyl of 1 to 5 carbon atoms or R''' and R'''' together with the α-carbon atom form a cyclopentane or cyclohexane ring, and R''' or R'''' can also be hydroxyalkyl of 1 to 4 carbon atoms and R'''' can also be phenyl, in the presence of an acidic catalyst, and removing the alcohol resulting from the trans-etherification.

2. An alkoxyalkylaminotriazine trans-etherification product as defined in claim 1, wherein the alkoxyalkylaminotriazine used is essentially hexamethoxymethylaminotriazine.

3. An alkoxyalkylaminotriazine trans-etherification product as defined in claim 1, wherein the β-hydroxyaldehyde used is hydroxypivalaldehyde.

4. An alkoxyalkylaminotriazine trans-etherification product as defined in claim 2, wherein the β-hydroxyaldehyde used is hydroxypivalaldehyde.

5. An alkoxyalkylaminotriazine trans-etherification product as defined in claim 1, which is obtained by reacting an alkoxyalkylaminotriazine of the formula (I) with from 0.5 to 4.5 moles, per mole of alkoxyalkylaminotriazine, of a β-hydroxyaldehyde of the formula (II).

* * * * *